United States Patent [19]
Eliash et al.

[11] Patent Number: 5,324,400
[45] Date of Patent: * Jun. 28, 1994

[54] ELECTRODE PRECONDITIONING METHOD FOR A PLATING BATH MONITORING PROCESS

[75] Inventors: Bruce M. Eliash; Nguyet H. Phan, both of Los Angeles; Frank A. Ludwig, Rancho Palos Verdes; Vilambi N. Reddy, Lakewood, all of Calif.

[73] Assignee: Hughes Aircraft Company, Los Angeles, Calif.

[*] Notice: The portion of the term of this patent subsequent to Mar. 29, 2011 has been disclaimed.

[21] Appl. No.: 986,846

[22] Filed: Dec. 4, 1992

[51] Int. Cl.$^5$ .............................................. G01N 27/26
[52] U.S. Cl. .................. 204/153.1; 204/402; 204/412; 204/434
[58] Field of Search ............ 204/402, 412, 434, 153.1; 205/81, 101, 102, 103, 104, 105

[56] References Cited
PUBLICATIONS

Tench et al., Cyclic Pulse Voltammetric Stripping Analysis of Acid Copper Plating Baths, Jun. 1984, pp. 831–834.

*Primary Examiner*—John Niebling
*Assistant Examiner*—Bruce F. Bell
*Attorney, Agent, or Firm*—M. E. Lachman; M. W. Sales; W. K. Denson-Low

[57] ABSTRACT

A method of preconditioning an electrode for use in a plating bath monitoring process. The method involves applying at least one anodic signal to an electrode in contact with the plating bath solution in order to yield a reproducibly clean and stabilized electrode surface, and then applying a plating signal to deposit a layer of metal on the anodically treated electrode. The resultant preconditioned electrode improves the accuracy and precision of subsequent voltammetric monitoring measurements for a variety of different plating baths. The method is easily integrated with and thereby enhances the capabilities of known voltammetric plating bath monitoring processes.

13 Claims, 4 Drawing Sheets

ELECTRODE PRECONDITIONING METHOD FOR A PLATING BATH MONITORING PROCESS

BACKGROUND OF THE INVENTION

1. Field of the Invention

The present invention relates generally to plating baths and methods for monitoring the constituents contained therein. More particularly, the present invention relates to a method for preconditioning an electrode used to monitor plating bath constituents.

2. Description of Related Art

A typical plating bath solution is comprised of a combination of several different electrochemical constituents. The specific constituents vary depending upon the type of plating bath, but in general can be broadly divided into what are commonly known as major constituents and minor, or trace, constituents. It has long been recognized that appropriate levels of both major and trace constituents must be maintained to consistently produce high quality, reliable plated material at low cost. The monitoring and control of plating baths is therefore a major concern to the electronics, automotive and general electroplating industries.

Voltammetric signal analysis provides an efficient means for monitoring a plating bath solution. One such monitoring process is described in U.S. Pat. No. 4,631,116, assigned to the present assignee. The method disclosed therein applies a combined ac and dc voltammetric signal to an electrode in contact with the plating solution to produce ac current spectra which indicate trace constituent concentration levels. In order to achieve accurate, repeatable and robust results, plating bath analysis methods such as these include a means for preconditioning the electrode to yield a reproducibly clean and reactive electrode surface. In U.S. Pat. No. 4,631,116, the electrode is pretreated by applying one or more anodic voltages for a certain period of time prior to the measurement of the ac spectra. The voltage and application time of the pretreatment signal are varied to determine the settings which provide the best measurement repeatability for a particular constituent.

For certain types of plating baths and constituents, however, anodic preconditioning alone may not produce adequate measurement accuracy and repeatability. In a chromium plating bath solution, for example, repeatable and robust results are difficult to obtain regardless of the voltage and duration of the anodic preconditioning signal. Similar problems may arise with other types of plating baths. In such a situation, the benefits of the monitoring process are lost as a result of inadequate electrode preconditioning.

As is apparent from the above, there presently is a need for a simple and versatile preconditioning method which improves monitoring accuracy and repeatability for a wide variety of plating baths and constituents. The method should provide an alternative preconditioning technique suitable for use in those situations where anodic preconditioning alone yields unsatisfactory results. Furthermore, the method should be compatible with existing voltammetric analysis systems, thereby expanding the measurement capability of those systems without requiring additional equipment.

SUMMARY OF THE INVENTION

In accordance with the present invention a method for preconditioning a plating bath monitoring system electrode is provided. The method is based upon the discovery that preconditioning an electrode using both anodic voltage and plating signals can enhance the accuracy and reproducibility of voltammetric monitoring techniques for certain types of plating baths and the constituents contained therein. The method involves first applying one or more anodic voltage signals to a working electrode in contact with the plating bath solution in order to remove adsorbed surface species and stabilize the platinum oxide interface, and then applying a plating signal to deposit a layer of metal onto the cleaned and stabilized electrode surface to produce the preconditioned electrode. Monitoring measurements can then be performed by applying voltammetric signals to the preconditioned electrode.

As a feature of the present invention, the method provides a simple and versatile electrode preconditioning technique. The method involves a two step process of anodic treatment and plating the electrode in order to improve the accuracy of the subsequent monitoring measurements. The preconditioning can be performed without removing the electrode from the solution, and the method can be repeated prior to each measurement without delaying the monitoring process.

As another feature of the present invention, the accuracy and repeatability of the resultant measurements for certain plating baths are significantly improved over those obtained using known preconditioning techniques. The present invention thus provides an alternative preconditioning technique for monitoring those plating baths for which anodic preconditioning alone does not yield optimal measurement accuracy.

As a further feature of the present invention, the method is easily integrated with known plating bath measurement equipment, thereby providing improved accuracy, precision, and expanded capabilities for plating bath monitoring systems without requiring additional equipment.

The above-discussed features and attendant advantages of the present invention will become better understood by reference to the following detailed description of the preferred embodiment and the accompanying drawings.

DESCRIPTION OF THE PREFERRED EMBODIMENT

The present invention is based upon the discovery that the accuracy of voltammetric plating bath analysis techniques can be improved by preconditioning the working electrode with both anodic voltage and plating signals. Although the following detailed description discusses only one exemplary voltammetric technique, it should be understood that the method of the present invention can be readily adapted for use with other ac and dc voltammetric techniques. The exemplary voltammetric analysis technique to which the method of the present invention is applied in this detailed description is disclosed in U.S. Pat. No. 4,631,116. The contents of this patent are hereby expressly incorporated by reference.

As was mentioned above, a chromium plating bath is one type of plating bath in which pretreating the electrode with an anodic signal alone limits the accuracy of subsequent measurements. Although the examples in the following description are directed to an exemplary chromium plating bath, it should be understood that this is not by way of limitation. The method of the present invention can also be applied to a wide variety of other plating baths.

Figure 1:
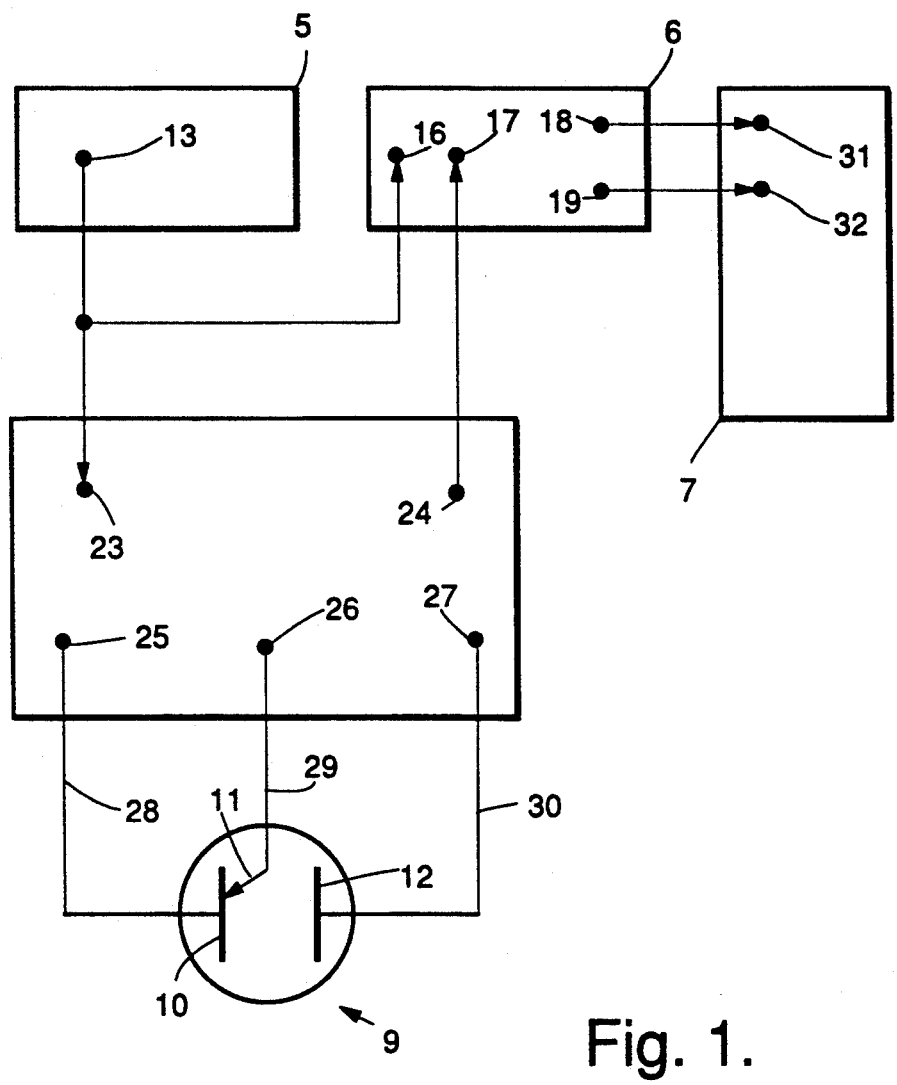
FIG. 1 is a schematic representation of a preferred embodiment for conducting the method in accordance with the present invention.

The schematic diagram of FIG. 1 illustrates a preferred embodiment of a voltammetric system used to conduct the method of the present invention. The system is capable of applying both preconditioning and voltammetric measurement signals to an electrode in contact with the plating bath solution. The plating bath solution is located within an electrochemical cell 9. The electrochemical cell 9 is preferably part of an electrochemical sensor submerged within the plating bath. A pump (not shown) can be used to draw the solution through the cell 9.

In the exemplary system of FIG. 1, the preconditioning signals of appropriate potential and duration are generated within potentiostat 8. Alternatively, an external dc waveform generator can be used. The preconditioning signals consist of one or more anodic signals, followed by a plating signal. Dc pulse waveforms are preferably used to clean the working electrode 10 by removing any adsorbed organic materials or other contaminants and to stabilize the platinum oxide surface. The anodic treatment yields a reproducible electrode surface for the subsequent plating step. The working electrode 10 is typically a platinum wire about 1 mm in diameter and about 1 cm long. The working electrode could also be constructed of other materials, such as gold. The anodic treatment may be performed by a single dc pulse or several dc pulses. Other types of cleaning signals, such as an anodic dc sweep could also be used.

The plating signal is used to deposit a layer of metal on the cleaned working electrode to a thickness of about a few microns. Deposited metals can be obtained from a variety of electroplating solutions, including but not limited to copper, iron, nickel, chromium, zinc, gold, silver, silver, lead, platinum, cadmium, tin, palladium, rhodium, indium, cobalt, and mixtures thereof. The plating signal is preferably a constant dc signal, either potentiostatic or galvanostatic, but any other plating signal which yields an adherent, smooth deposit could also be used. Alternative plating signals include pulsed and periodic reversed dc and ac superimposed on dc. The preconditioning signals may be applied immediately prior to each voltammetric measurement. Alternatively, the signals could be applied at regular predetermined intervals throughout the monitoring process. The parameters of the preconditioning signals will be discussed in further detail below.

The preconditioning signals are generated within the potentiostat and applied from potentiostat port 25 to the working electrode 10 in the electrochemical cell 9 via line 28. In the potentiostatic mode, the potentiostat 8 serves to insure that the amplitude of the preconditioning and measurement waveforms does not vary as a result of variations in current flow through the electrochemical cell. The electrochemical cell 9 also contains a counter electrode 12 and a standard calomel reference electrode 11. The reference electrode 11 and counter electrode 12 are connected to potentiostat ports 26, 27 via lines 29, 30, respectively.

After the preconditioning signals have been applied to the working electrode 10, the waveform generator 5 produces an ac voltammetric signal which is applied to the external input 23 of potentiostat 8 and to the reference input 16 of a lock-in amplifier 6. The potentiostat 8 superimposes the ac voltammetric signal upon an appropriate dc voltage sweep signal generated within the potentiostat. The combined ac and dc voltammetric signal is applied to the working electrode 10 to measure plating bath constituent concentrations.

A response current is generated between the working electrode 10 and the counter electrode 12 in response to the voltammetric excitation signal. Peaks in the response ac current spectra indicate plating bath constituent concentration levels. The response current passes back through potentiostat 8, from potentiostat output 24 to the signal input 17 of lock-in amplifier 6 and to the strip chart recorder 7. The lock-in amplifier resolves a desired response current into its in-phase and quadrature components. In the exemplary response current spectra shown in FIGS. 2 through 7 the second harmonic of the ac portion of the response signal provided the best measurement resolution.

The in-phase component of the response current second harmonic is then passed from in-phase output 18 of lock-in amplifier 6 to display signal input 31 of strip chart recorder 7. Similarly, the quadrature component is passed from quadrature output 19 of lock-in amplifier 6 to a second display signal input 32 of strip chart recorder 7. The strip chart recorder displays the in-phase and the quadrature components of the ac portion of the response current as a function of the dc sweep portion of the response current, as shown in FIGS. 2 through 7. These displays represent unique spectra which indicate particular constituent concentration levels within the plating bath solution.

The specific equipment used in the exemplary system of FIG. 1 included a Wavetek Model 188 waveform generator, a PAR 273 potentiostat, and a PAR 5208 lock-in amplifier. The Wavetek waveform generator is available from Wavetek San Diego, Inc., of San Diego, Calif. and the PAR equipment is available from Princeton Applied Research, of Princeton, N.J.

In order to optimize the accuracy and sensitivity of the response current spectra to detection of a particular plating bath constituent, the potential and duration of the preconditioning signals should be independently varied. Other test parameters applicable to the exemplary system of FIG. 1 may also be varied, including: 1) type of ac voltammetric waveform (i.e., sinusoidal, square, triangular, etc.); 2) ac voltammetric signal amplitude and frequency; 3) dc voltammetric sweep signal voltage range and sweep rate; 4) ac response current harmonic measured (i.e., first (or fundamental), second, etc.); 5) ac response current phase angle measured; and 6) hydrodynamic conditions (i.e., degree of agitation).

The preconditioning signal parameters were independently varied to determine appropriate ranges for monitoring exemplary major and trace constituents in a variety of different plating baths. In addition, the other system parameters applicable to the exemplary voltammetric technique of FIG. 1 were also independently varied to determine optimal settings which, when used in conjunction with the preconditioning signals of the present invention, produced the most accurate and repeatable measurement spectra. It should be emphasized that the preconditioning signal parameter range limits described below are average and that the present invention may produce useful results with parameter values outside the specified ranges. In applying the method of the present invention to other plating bath measurement systems, the preconditioning signals, as well as the other system parameters applicable to the particular technique, should be varied to determine appropriate parameter settings.

In general, certain ranges of the preconditioning signal parameters are particularly well-suited for preparing the electrode for monitoring both major and trace constituent concentrations in accordance with the preferred embodiment of FIG. 1. All voltages discussed herein are with respect to a saturated calomel electrode. The anodic treatment signal is a dc potential of about 2 to 3.5 volts, and is applied to the working electrode 10 for about 5 to 40 seconds. This generally is sufficient to remove substantially all adsorbed species from the electrode surface and stabilize the platinum oxide interface. A plating signal is then applied to the cleaned working electrode to deposit a layer of metal from the chromium plating bath onto the electrode surface. The plating signal used is preferably a dc signal having a cathodic amplitude sufficient to plate the metal and a duration of about 10 to 60 seconds. Preconditioning signals within the above ranges can improve the accuracy and precision of the resultant measurement spectra for a variety of plating baths. Further refinements within the above ranges can be made for particular plating baths or constituents.

The method as described above has been applied to the detection of major and trace constituents within an exemplary chromium plating bath obtained from M & T Chemicals, Inc. of Rahway, N.J., as HCR-840 and CR-842. Examples of the optimization of the electrode preconditioning method of the present invention using the preferred embodiment of FIG. 1 are as follows.

A major constituent within a chromium plating bath is chromic acid. Ac current spectra of the type shown in FIGS. 2 and 3 were obtained for chromic acid concentrations in a chromium bath. Prior to each measurement, the working electrode was preconditioned using the two step preconditioning process of the present invention. First, an anodic potential of 2.4 volts was applied to the working electrode for a period of about 20 to 36 seconds. Second, a dc plating signal was used to deposit a layer of metal on the cleaned electrode. The plating signal had a potential of about $-1.1$ to $-1.5$ volts and a duration of about 40 to 60 seconds.

Figure 3:
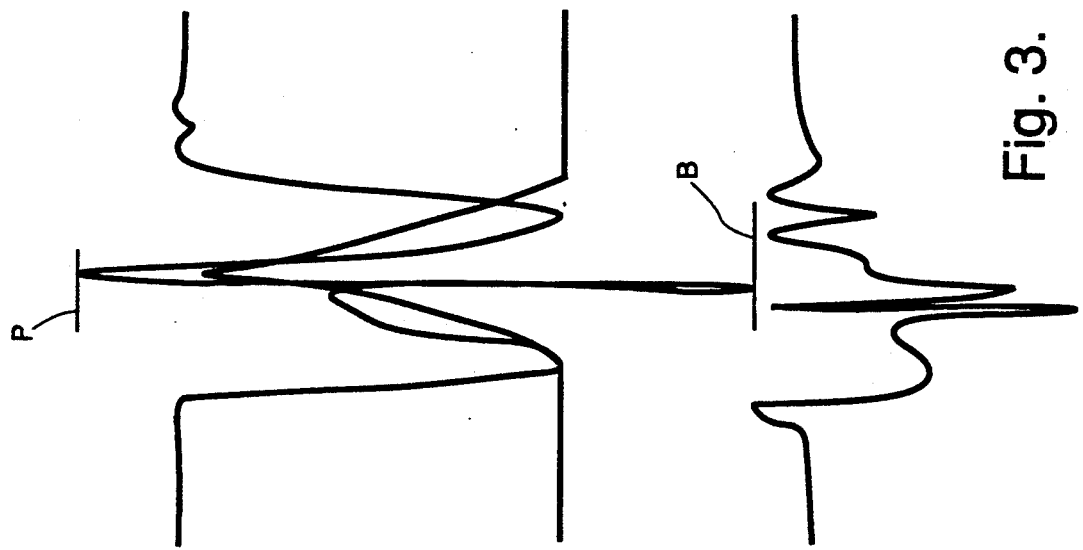
FIGS. 2–7 show exemplary ac current spectra obtained using a working electrode preconditioned in accordance with the method of the present invention to monitor the concentration of various chromium plating bath constituents.
Figure 2:
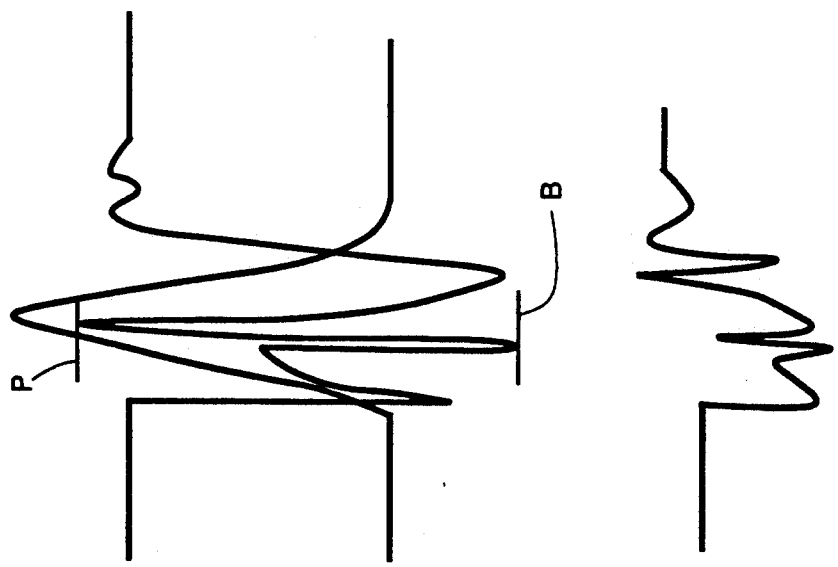

After the working electrode was preconditioned, ac measurement spectra were obtained as shown in FIGS. 2 and 3. In order to obtain these spectra, an ac signal with an amplitude of about 25 mv root mean squared (rms) amplitude and a frequency of about 1000 Hz was superimposed on a dc sweep signal and applied to the working electrode. The dc signal was swept from about 0.0 to about $-1.5$ volts and reversed to about 0.0 volts at a rate of about 50 mv/sec. The most sensitive spectral peak was found on the in-phase component of the second harmonic ac response signal, measured using a phase angle offset of about 10 degrees. During the measurement, the solution within the electrochemical cell was stirred continuously. The solution was maintained at a temperature of about 60° C.

The ac spectra shown in FIG. 2 were obtained by applying the above signals to a chromium plating bath solution containing 225 g/liter chromium trioxide (chromic acid), 1 g/liter sulfate catalyst and 4 g/liter silicofluoride catalyst. The height of spectral peak P, measured from baseline B, measures about 180 mv and corresponds to a concentration of 225 g/liter of chromic acid within the plating bath solution. In FIG. 3 the effect of increasing the concentration of chromic acid within the solution of FIG. 2 to 255 g/liter is shown. The resulting ac response peak measured 225 mv, reflecting the increase in the chromic acid content of the solution. The measurements were performed for several other concentrations of chromic acid. When using the above identified pretreatment and measurement signal parameters, the sensitivity of the detection of chromic acid concentration was about 1.5 mv/(g/liter chromic acid). A one g/liter change in the concentration of chromic acid in the solution would thus result in a change in the peak P voltage of about 1.5 mv.

In another example, optimal preconditioning and measurement signal parameters have been determined for detecting the concentration of silicofluoride catalyst, a trace constituent in the chromium plating bath. Prior to each measurement, the working electrode was preconditioned in accordance with the method of the present invention. A dc signal with anodic potential of 2.4 volts was first applied to the electrode for a period of about 20 to 36 seconds. The cleaned electrode was then plated using a dc plating signal with an amplitude of about $-1.1$ to $-1.5$ volts applied for a period of about 20 to 36 seconds.

To generate exemplary measurement spectra indicative of silicofluoride concentration, an ac signal of 25 mv rms amplitude and 1000 Hz frequency was superimposed on a dc signal swept from 0 volts to $-1.5$ volts and reversed to 0 volts at a rate of 50 mv/sec. The combined ac and dc voltammetric signal was then applied to the working electrode, resulting in the response current spectra shown in FIGS. 4 and 5. The most sensitive spectral peak was found on the quadrature component of the second harmonic ac response signal, measured at a phase angle offset of 20°. The solution was stirred continuously during the measurement and maintained at a temperature of about 60° C.

Figure 5:
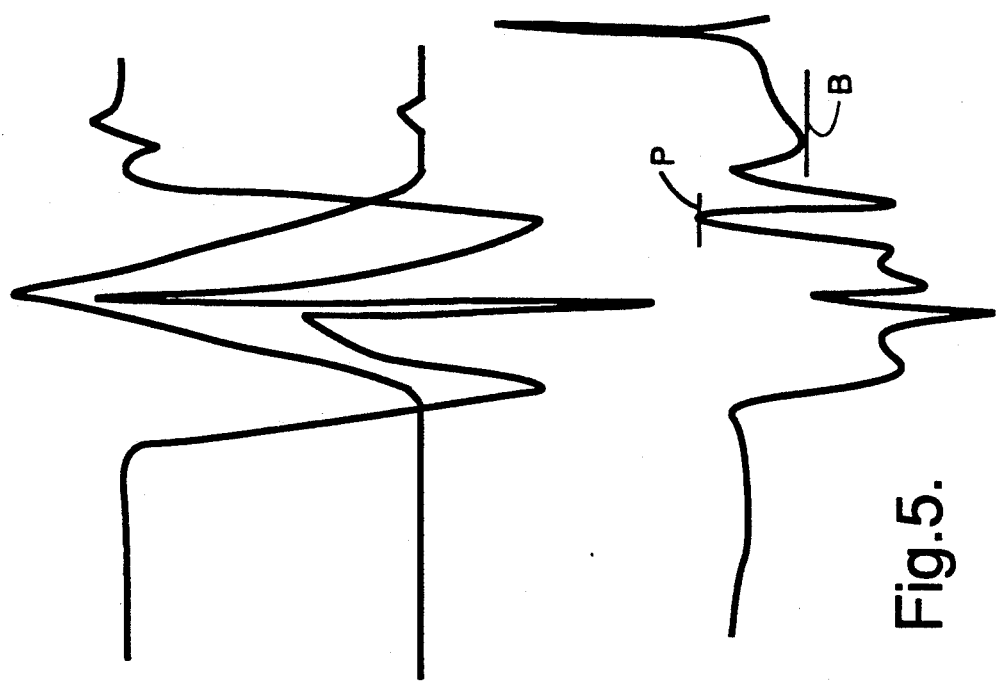
Figure 4:
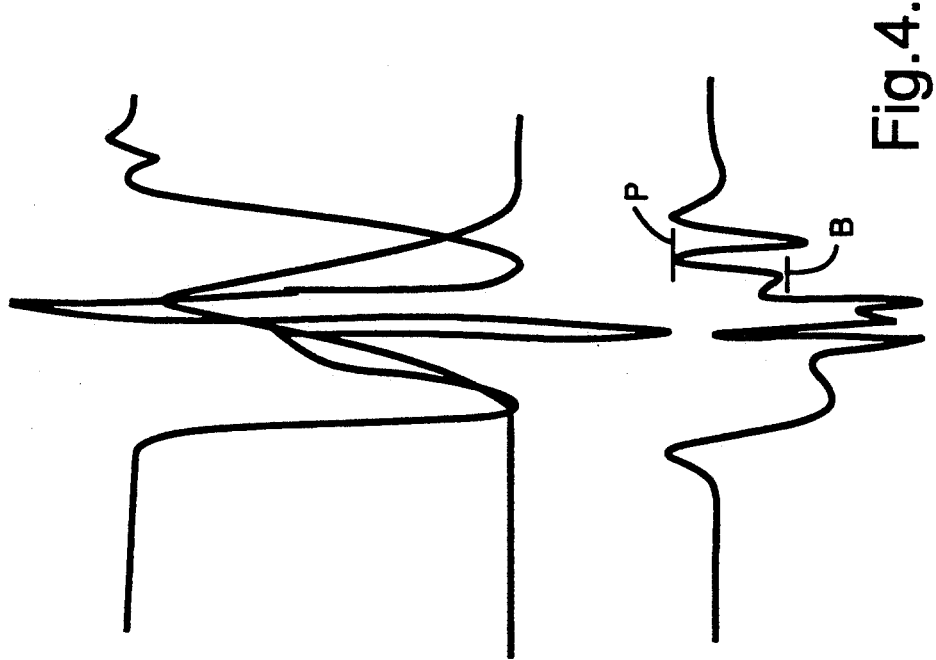

The spectra of FIG. 4 result from applying the preconditioning and measurement signals described above to the solution of FIG. 2 but with silicofluoride catalyst content of 2 g/liter. The resulting peak P, measured from baseline B, of the quadrature component of the ac portion of the response signal measured 25 mv. The effect of increasing the silicofluoride catalyst content of the solution of FIG. 4 from 2 g/liter to 4 g/liter silicofluoride is shown in FIG. 5. The height of peak P increases to 45 mv. Applying the method to solutions with different concentrations of silicofluoride produced consistent results. Silicofluoride detection sensitivity using a working electrode preconditioned in accordance with the present invention is thus about 10 mv/(g/liter of silicofluoride catalyst).

In a final example, optimal preconditioning and measurement signal parameters have been determined for monitoring sulfate catalyst concentration in the exemplary chromium plating bath. Prior to each measurement, an anodic potential of about 2.4 volts was applied to the working electrode for a period of about 20 seconds in order to clean the working electrode. The cleaned working electrode was then plated using a dc plating signal with a potential of about $-1.1$ volts. The plating signal was applied for about 40 seconds.

Measurement spectra indicative of sulfate catalyst concentration were then obtained using an ac signal of 25 mv rms amplitude and 2000 Hz frequency superimposed on a dc signal swept from 0 to −1.5 volts and reversed to 0 volts at a rate of 50 mv/sec. The most sensitive spectral peak was found on the in-phase component of the second harmonic ac response signal, measured at a phase angle offset of 20 degrees. The solution was maintained at a temperature of 60° C. during the measurements.

Figure 7:
Figure 6:
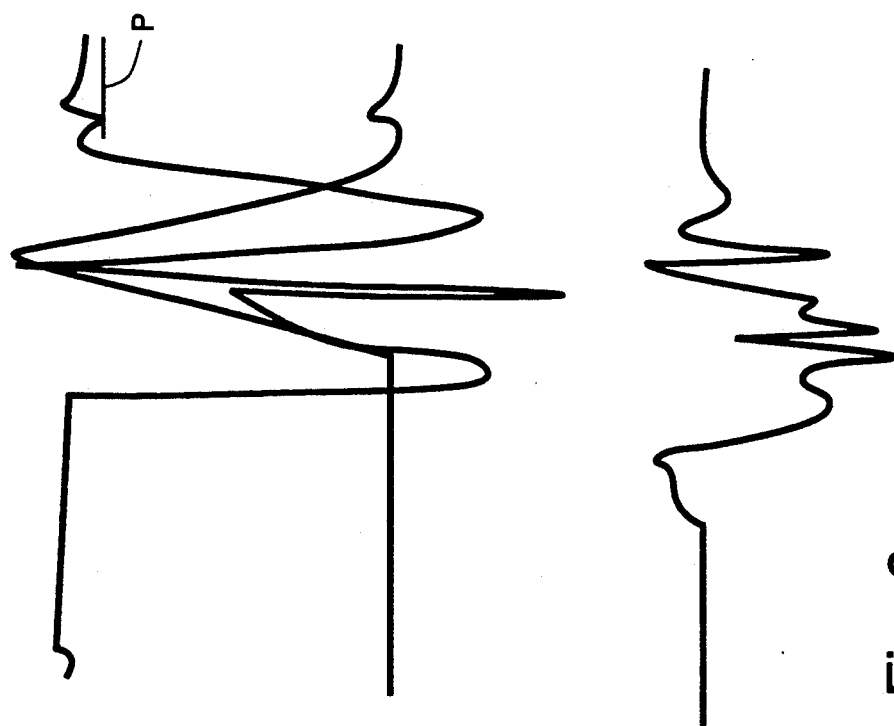

The preconditioning and measurement signals described above were applied to the solution of FIG. 2. The resultant spectra are shown in FIG. 6. The peak P of the in-phase component of the ac response signal occurs at the end of the plating portion of the dc swept signal and measures 6.3 mv. The effect of increasing the concentration of sulfate catalyst in the solution of FIG. 6 from 1 g/liter to 2 g/liter is shown in the spectra of FIG. 7. The height of peak P increased to 37.5 mv. Further measurements using other concentrations of sulfate catalyst yielded similar results. The sensitivity of this method as applied to the trace constituent sulfate catalyst in a chromium plating bath is thus about 31.2 mv/(g/liter of sulfate catalyst).

As can be seen in FIGS. 2 through 7, the method of the present invention produces reliable and repeatable spectra with easily distinguishable peaks corresponding to the concentration levels of various constituents. These spectra can be used in conjunction with an overall plating bath analysis system which monitors and maintains proper levels of major and trace constituents within various plating baths in real time without removing fluid from the plating tank.

Although the above description has been limited to analysis of exemplary major and trace constituents using an exemplary ac voltammetry technique, this is by way of illustration and not limitation. It will be understood by those skilled in the art that the electrode preconditioning method of the present invention may be applied to other plating bath solutions or used in conjunction with other voltammetric monitoring techniques without deviating from the scope of the invention, which is limited only by the appended claims.

What is claimed is:

1. A method of preconditioning a working electrode used for monitoring constituents in a plating bath solution, said method comprising the steps of:

applying at least one anodic signal to said working electrode positioned within said solution, said anodic signal having a potential and applied for a period of time such that a reproducibly clean and stabilized surface is formed on said working electrode, producing an anodically treated working electrode; and applying a plating signal to said anodically treated working electrode to deposit a layer of metal onto said anodically treated working electrode;

repeating said steps of applying anodic and plating signals to produce a preconditioned working electrode;

wherein voltammetric measurement signals can then be applied to said preconditioned working electrode to accurately monitor particular constituents within said plating bath.

2. The method of claim 1 wherein said plating signal is a pulsed dc, periodic reversed dc or ac superimposed on dc signal.

3. The method of claim 1 wherein said anodic signal has a potential of about 2 to 3.5 volts and is applied for about 5 to 40 seconds.

4. The method of claim 1 wherein said working electrode is formed from a material selected from the group consisting of platinum and gold.

5. The method of claim 1 wherein said layer of metal deposited on said working electrode is selected from the group consisting of copper, iron, nickel, chromium, zinc, tin, gold, silver, lead, platinum, cadmium, palladium, rhodium, indium, cobalt and mixtures thereof.

6. The method of claim 1 wherein said plating signal is a constant dc signal, either potentiostatic or galvanostatic, having a cathodic amplitude sufficient to plate the metal and a duration of about 10 to 60 seconds.

7. The method of claim 1 wherein said plating bath is a chromium plating bath and further wherein said chromium bath contains several constituents.

8. The method of claim 7 wherein one of said constituents in said chromium plating bath is chromic acid and further wherein said anodic signal has a potential of about 2.4 volts and is applied for about 20 to 36 seconds.

9. The method of claim 7 wherein one of said constituents in said chromium plating bath is silicofluoride catalyst and further wherein said anodic signal has a potential of about 2.4 volts and is applied for about 20 to 36 seconds.

10. The method of claim 7 wherein one of said constituents in said chromium plating bath is sulfate catalyst and further wherein said anodic signal has a potential of about 2.4 volts and is applied for about 20 seconds.

11. The method of claim 8 wherein said plating signal is a dc signal having an amplitude of about −1.1 to −1.5 volts and a duration of about 40 to 60 seconds.

12. The method of claim 9 wherein said plating signal is a dc signal having an amplitude of about −1.1 to −1.5 volts and a duration of about 20 to 36 seconds.

13. The method of claim 10 wherein said plating signal is a dc signal having an amplitude of about −1.1 volts and a duration of about 40 seconds.

* * * * *